United States Patent
Wang et al.

(10) Patent No.: US 10,939,894 B2
(45) Date of Patent: Mar. 9, 2021

(54) ACOUSTIC STREAMING FOR FLUID POOL DETECTION AND IDENTIFICATION

(71) Applicant: KONINKLIJKE PHILIPS N.V., Eindhoven (NL)

(72) Inventors: Shougang Wang, Ossining, NY (US); Balasundar Iyyavu Raju, North Andover, MA (US); Shiwei Zhou, Yorktown Heights, NY (US); Jingping Xu, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 62 days.

(21) Appl. No.: 15/503,812

(22) PCT Filed: Aug. 12, 2015

(86) PCT No.: PCT/IB2015/056141
§ 371 (c)(1),
(2) Date: Feb. 14, 2017

(87) PCT Pub. No.: WO2016/024236
PCT Pub. Date: Feb. 18, 2016

(65) Prior Publication Data
US 2017/0273658 A1 Sep. 28, 2017

Related U.S. Application Data

(60) Provisional application No. 62/037,194, filed on Aug. 14, 2014.

(51) Int. Cl.
*A61B 8/06* (2006.01)
*A61B 8/08* (2006.01)
(Continued)

(52) U.S. Cl.
CPC .............. *A61B 8/06* (2013.01); *A61B 8/08* (2013.01); *A61B 8/085* (2013.01); *A61B 8/0808* (2013.01);
(Continued)

(58) Field of Classification Search
CPC ....... A61B 8/488; A61B 8/08; A61B 5/02007; A61B 8/06; A61B 8/0891; A61B 8/00;
(Continued)

(56) References Cited

U.S. PATENT DOCUMENTS

| 5,487,387 A | 1/1996 | Trahey et al. |
|---|---|---|
| 5,961,460 A | 10/1999 | Guracar et al. |

(Continued)

FOREIGN PATENT DOCUMENTS

EP  0882426 A2  12/1998

OTHER PUBLICATIONS

Zagrodsky, et al., "Automated Detection of a Blood Pool in Ultrasound Images of Abdominal Trauma", Ultrasound in Medicine & Biology, vol. 33, No. 11, pp. 1720-1726.
(Continued)

*Primary Examiner* — Amelie R Davis

(57) ABSTRACT

Ultrasound-based acoustic streaming for deciding whether material is fluid is dependent upon any one or more of a variety of criteria. Examples are displacement, speed, temporal or spatial flow variance, progressive decorrelation, slope or straightness of accumulated signal to background comparisons over time, and relative displacement to adjacent soft tissue. Echogenicity-based area identification is combinable with the above movement characteristic detection in the deciding. Fluid pool identification is performable from the area-limited acoustic streaming testing and ultrasound attenuation readings. Candidates from among the areas are screenable based on specific shapes or bodily
(Continued)

organs detected. Natural flow can be excluded from streaming detection by identification of blood vessels. Processing for each FAST ultrasound view, or for the entire procedure, is performable automatically, without need for user intervention or with user intervention to identify suspected areas.

11 Claims, 10 Drawing Sheets

(51) Int. Cl.
*A61B 8/00* (2006.01)
*G01S 7/52* (2006.01)
*G01S 15/89* (2006.01)
*G06T 7/12* (2017.01)

(52) U.S. Cl.
CPC ............ *A61B 8/4427* (2013.01); *A61B 8/485* (2013.01); *A61B 8/488* (2013.01); *A61B 8/5223* (2013.01); *G01S 7/52022* (2013.01); *G01S 7/52036* (2013.01); *G06T 7/12* (2017.01); *A61B 8/4477* (2013.01); *A61B 8/486* (2013.01); *A61B 8/5246* (2013.01); *A61B 8/5276* (2013.01); *G01S 15/8915* (2013.01); *G06T 2207/10132* (2013.01); *G06T 2207/20036* (2013.01); *G06T 2207/20152* (2013.01); *G06T 2207/30101* (2013.01)

(58) Field of Classification Search
CPC ..... A61B 8/4444; A61B 8/0808; A61B 8/085; A61B 8/4427; A61B 8/4477; A61B 8/485; A61B 8/486; A61B 8/5223; A61B 8/5246; A61B 8/5276; G01S 15/8915; G01S 7/52022; G01S 7/52036; G06T 2207/10132; G06T 2207/20036; G06T 2207/20152; G06T 2207/30101; G06T 7/12

See application file for complete search history.

(56) References Cited

U.S. PATENT DOCUMENTS

| | | |
|---|---|---|
| 2005/0089205 A1 | 4/2005 | Kapur et al. |
| 2006/0116579 A1 | 6/2006 | Li et al. |
| 2009/0221902 A1 | 9/2009 | Myhr |
| 2010/0168566 A1 | 7/2010 | Bercoff et al. |
| 2011/0178444 A1 | 7/2011 | Slayton et al. |
| 2013/0066204 A1* | 3/2013 | Fan ............ A61B 8/0858 600/438 |
| 2013/0079641 A1 | 3/2013 | Zwim |
| 2013/0245426 A1* | 9/2013 | Lee ............ A61B 6/502 600/411 |
| 2014/0213901 A1* | 7/2014 | Shackelford ........ A61B 8/085 600/437 |
| 2016/0239959 A1* | 8/2016 | Blackbourne ........ G06K 9/46 |

OTHER PUBLICATIONS

Scolla, et al., "Analysis of cross-correlation coefficiencies for subcutaneous blood signal detection by ARFI Imaging", Ultrasonics Symposium, 2009 IEEE International, IEEE, Piscataway, NJ, USA, Sep. 20, 2009 pp. 1883-1886.

Xuegong et al., "Quantitive investigation of of acoustic streaming blood", The Journal of the Acoustical Society of America, American Institute of Physics for the Acoustical Society of America, New York, NY, US, vol. 111, No. 2, Feb. 1, 2002, pp. 1110-1121.

Shi X, et al., "Color Doppler detection of acoustic streaming in a hematoma model", Ultrasound in Medicine and Biology, New York, NY, US, vol. 27, No. 9, Sep. 1, 2001, pp. 1255-1264.

* cited by examiner $$426 \longrightarrow \frac{\overline{|v_i - v_j|} \ (\forall \ I \leq i < j \leq N)}{\overline{|v_k|} \ (\forall \ I \leq k \leq N)} < T_R \ ? \quad 428$$

ACOUSTIC STREAMING FOR FLUID POOL DETECTION AND IDENTIFICATION

This application is the U.S. National Phase application under 35 U.S.C. § 371 of International Application No. PCT/IB2015/056141, filed on Aug. 12, 2015, which claims the benefit of U.S. Provisional Application Ser. No. 62/037,194, filed Aug. 14, 2014. These applications are hereby incorporated by reference herein.

FIELD OF THE INVENTION

The present invention relates to detecting a fluid and, more particularly, to detecting a fluid by use of acoustic power.

BACKGROUND OF THE INVENTION

Trauma is the sixth leading cause of death worldwide, accounting for 10% of all mortality, and is a serious public health problem with significant social and economic costs. Trauma is an injury to living tissue by an extrinsic force such as: a body wound or shock produced by sudden physical injury as from violence or accident; or a physical wound or injury such as from a blow, which is often seen in abdominal trauma. Trauma is commonly divided into blunt trauma and penetrating trauma. Blunt trauma is a common injury affecting intra-abdominal and pelvic structures where the liver and spleen are the most injured organs. Blunt trauma is the leading cause of traumatic death in the United States.

There are two kinds of bleeding: (a) internal bleeding where blood leaks from blood vessels inside the body; and (b) external bleeding either through a natural opening like the vagina, mouth, nose, ear or anus, or through a break in the skin. Typically, the total intravascular blood volume is about 5 liters for a 70 kilogram (kg) healthy human, and the cardiac output is 70 milliters (ml) per beat, or about 5 liters per minute at rest. He/she can lose about 10-15% of total blood volume without serious medical difficulties. Blood pool will develop only in case (a), doing so at a location where blood is still inside the human body but outside of circulation.

There are a few approaches for blood pool detection, such as: computed tomography (CT) or magnetic resonance imaging (MRI), as well as ultrasound. CT is the gold standard for blood pool and active bleeding detection. However, it is impractical to use CT/MRI for monitoring a dynamic process due to relatively high cost. In addition, CT entails exposing the patient and clinicians to ionizing radiation. Ultrasound imaging is widely used for blood pool detection. Even a small amount of 20 to 50 ml is visible to an experienced ultrasound doctor or sonographer. However, since the sensitivity of ultrasound to free fluid varies with the amount of fluid present, it is difficult for the inexperienced user to detect that small of an amount of blood pool. While as little as 100 ml of fluid can be detected in some cases when multiple views are obtained, the examination is most sensitive when there exist 500 cc or more.

Blood pool detection is very important for bedside diagnosis of traumatic patients.

However, most clinical approaches used at present are based on visual observation of ultrasound images, which is time consuming and leads to outcomes that are heavily dependent on operator skill and experience.

The major problem for ultrasound examination is the need for advanced training and its accuracy is highly operator dependent.

Although the FAST (Focused Assessment with Sonography in Trauma) protocols tend to streamline the process of quick examination of trauma patients in the emergency room by relatively untrained users, a significant amount of training is still necessary and the above-noted shortcomings are still present.

Acoustic streaming can be described as the bulk movement of fluid in a sound field created by transfer of energy from the acoustic wave to the medium due to absorption and reflection.

U.S. Pat. No. 5,487,387 to Trahey is directed to distinguishing between a solid mass and a fluid filled cyst, since a cancerous tumor will contain a solid mass. However, it might also contain circulating blood. Trahey ultrasonically tests, with low intensity pulses, a pre-identified lesion, in a preliminary procedure, to detect vascular blood flow within the lesion. This avoids the situation of acoustic streaming in the subsequent actual testing being mistakenly detected when the flow was actually vascular, and a tumor was actually present.

Then, in the actual ultrasonic testing, Trahey applies acoustic power to determine the presence or absence of movement of fluid and its direction, and whether the tissue is solid, so that a decision can be made on whether to perform a biopsy. To detect whether a solid is present, Trahey sends a combination of push and tracking pulses. Trahey determines whether there is acoustic streaming, by whether the two-way time of flight of a tracking pulse is longer or shorter than a reference time of flight.

SUMMARY OF THE INVENTION

What is proposed herein below addresses one or more of the above concerns.

What is proposed herein relates to assessing whether material that is remotely located in an ultrasound medium is fluid, and whether the fluid is stationary. This challenge is met through the application of acoustic streaming testing. The application may be selective and adaptable to assist medical practitioners in diagnosis, particularly in emergency trauma situations.

One of the advantages of what is proposed herein below is that a patient's torso, or another part of the body such as the cranium, can be scanned for blood pool, utilizing ultrasound which is a relatively inexpensive, fast, safe, and convenient imaging modality. In remote and dangerous areas, ultrasound, as an imaging mode, has the advantage of portability and compactness. Ultrasound pulses are applied to induce acoustic streaming and to detect and measure any resulting movement of body tissue.

A further beneficial aspect is limiting the total power expenditure by the relatively high powered ultrasound pulses utilized for acoustic streaming. In particular, advanced image processing of B-modes ultrasound images can be used to reduce the field of search for blood pool. Reducing the power requirement allows for the use of tablet ultrasound scanners. These are very portable, maneuverable, and practical for medical emergencies. In remote and dangerous areas, lack of a high-bandwidth communication channel makes a self-contained system a practical requirement. Also, by reducing the field of search to within hypoechoic regions, false positives in pool detection are avoided. In addition, the reduced power expenditure allows for locally increasing the streaming push power in order to improve sensitivity of blood pool detection. The latter applies to low power and higher power systems. Additionally, B-mode image resolution is typically high compared to that for parametric images solely constructed using streaming motion data. Therefore, the use of echogenicity data contributes to achievement of higher resolution, resulting in the detection of smaller volumes of blood pool from internal bleeding.

As an added benefit, the potentially adverse effects of respiration and heartbeat on acoustic streaming detection can be eliminated efficiently. In particular, reliance on detection of tissue displacement, to infer the existence of acoustic streaming, can be impacted by these types of background motion. Motion gating or compensation is one solution, but slows down the medical procedure.

A technique proposed herein below as fluid/blood pool identification for suspected areas within the B-scan ultrasound image is effected by the following steps:
(1) identifying dark areas for possible fluid/blood pool through advanced image processing techniques (for example, feature extraction);
(2) inducing acoustic streaming only on these detected possible dark areas (for example, if the number of detected possible blood pools is 3, then acoustic streaming is applied to only 3 areas, usually to the middle of each of the detected area(s)); and
(3) after the acoustic streaming phase, an immediately-following tracking phase identifies characteristic parameters for the dark and surrounding background soft tissue. These characteristic parameters could be a) relative motion (for example: displacement, velocity, correlation coefficient (CC)), b) turbulence, i.e, spatio-temporal variation of fluid velocity, c) ultrasound attenuation, etc. If any characteristic parameter value exceeds its threshold, then the dark area is marked as fluid/blood pool, and the boundary of the fluid/blood pool is determined from a B-scan image. Otherwise, the detected area is deemed to be fat or something other than fluid/blood pool.

Since the acoustic streaming which operates by pushing is applied only to a specified area (i.e., dark area) and in a specified direction, the acoustic streaming produces a distinguishably stronger motion in the area than in background soft tissue (breath motion being a major issue for background soft tissue). Either a single characteristic parameter, or a combination of proposed single characteristic parameters, are usable in the fluid/blood pool identification.

As just mentioned, a technique proposed herein below detects, via spatial and/or temporal variation of flow speeds, turbulence in the tissue subjected to acoustic power for detecting acoustic streaming. The turbulence occurs in liquid but not in solid matter. Accordingly, the need for motion gating and compensation is eliminated, and blood pool detection is performed with greater speed and efficiency, especially important in a medical emergency.

In an aspect of what is proposed herein, an apparatus that decides whether material is fluid includes an ultrasound image acquisition system for deciding whether material that is in an ultrasound medium is fluid. The system issues an acoustic wave to cause bulk movement of the fluid in a sound field created by transfer of energy from the wave. The system, via pulsed acoustic power, induces, in the fluid, flow speeds that vary spatially and temporally. An acoustic streaming analysis processor, responsive to the system subjecting the material to the acoustic power, computes, as an estimate for the material, an indicator of speed and/or temporal variance of speed and/or spatial variance of speed. The processor performs the deciding based on the estimate.

In another aspect, a fluid pool identification apparatus includes the above-mentioned ultrasound image acquisition system. The apparatus further includes: a) an image segmentation module configured for, based on echogenicity evidenced in an ultrasound image of material subjected to an acoustic wave, identifying an area depicted in the image; and b) a user interface with the apparatus being designed for receiving, via the interface, user input for identification of the area; detecting a characteristic of movement occurring in an area the apparatus distinguishes based on correspondingly echogenicity or the input received; and considering a result of correspondingly the identifying or the receiving, together with a result of the detecting, in deciding whether an area is a fluid pool. The word "module" as used in this patent application is intended to broadly refer to any one or combination of hardware, software and firmware. The detecting may occur before or after the corresponding identifying or receiving.

In yet another aspect, an apparatus for determining whether material is liquid includes the above-described ultrasound image acquisition system, and an acoustic streaming analysis processor configured for: responsive to the system subjecting the material to the acoustic power, tracking the material; deriving a correlation coefficient based on a result of the tracking; comparing the coefficient to a reference value; and deciding, based on an outcome of the comparison, whether the tissue is fluid.

In what is also an aspect, an acoustic streaming apparatus includes an ultrasound image acquisition system, and an acoustic streaming analysis processor configured for identifying an imaging depth range based on intensity of echoes from acoustic power applied via the system. The processor is further configured for repeatedly detecting, both within the range and outside, accumulated displacement caused by the applied power; repeatedly comparing accumulated displacement within the range to that outside the range; determining a graph of values corresponding to the comparisons; and deciding, based on straightness and/or slope of the graph, whether material within the range is liquid.

In a yet further aspect, a medical apparatus for detecting induced acoustic streaming includes an ultrasound image acquisition system for issuing pulsed acoustic power to cause bulk movement of fluid in a sound field. The apparatus further includes: a) an image segmentation module for detecting, and defining, a hypoechoic area depicted in an ultrasound image; and/or b) a user interface, the apparatus being configured for receiving, from the interface, user input for identification of the area. The apparatus is configured for automatically, without the need for user intervention, detecting soft tissue in a body region that adjoins the area; the issuing both to the area and the tissue; comparing the area and the tissue as to relative motion from the issuing; and deciding, based on the comparison, whether the issuing has induced acoustic streaming.

In one still further aspect, an ultrasound acoustic streaming apparatus includes an ultrasound image acquisition system comprising an ultrasound transducer and a remote ultrasound transducer and/or a remote ultrasound-reflector. The apparatus further includes an image analysis system configured for using the acquisition system for performing both acoustic streaming testing and ultrasound attenuation measurement, for combining respective outcomes of the testing and measurement, and for, based on the combination, localizing a blood pool.

In other aspects, computer readable media, as described in further detail herein below, are designed for providing computer instructions for operating any one or combination of the above-described apparatuses.

All of the above-mentioned apparatuses are configurable to operate, in carrying out their respective above-described respective functions, automatically, without the need for user intervention.

Details of the novel, acoustic-streaming-based liquid, and blood pool, detection and localization technology are set forth further below, with the aid of the following drawings, which are not drawn to scale.

DETAILED DESCRIPTION OF EMBODIMENTS

Figure 1:
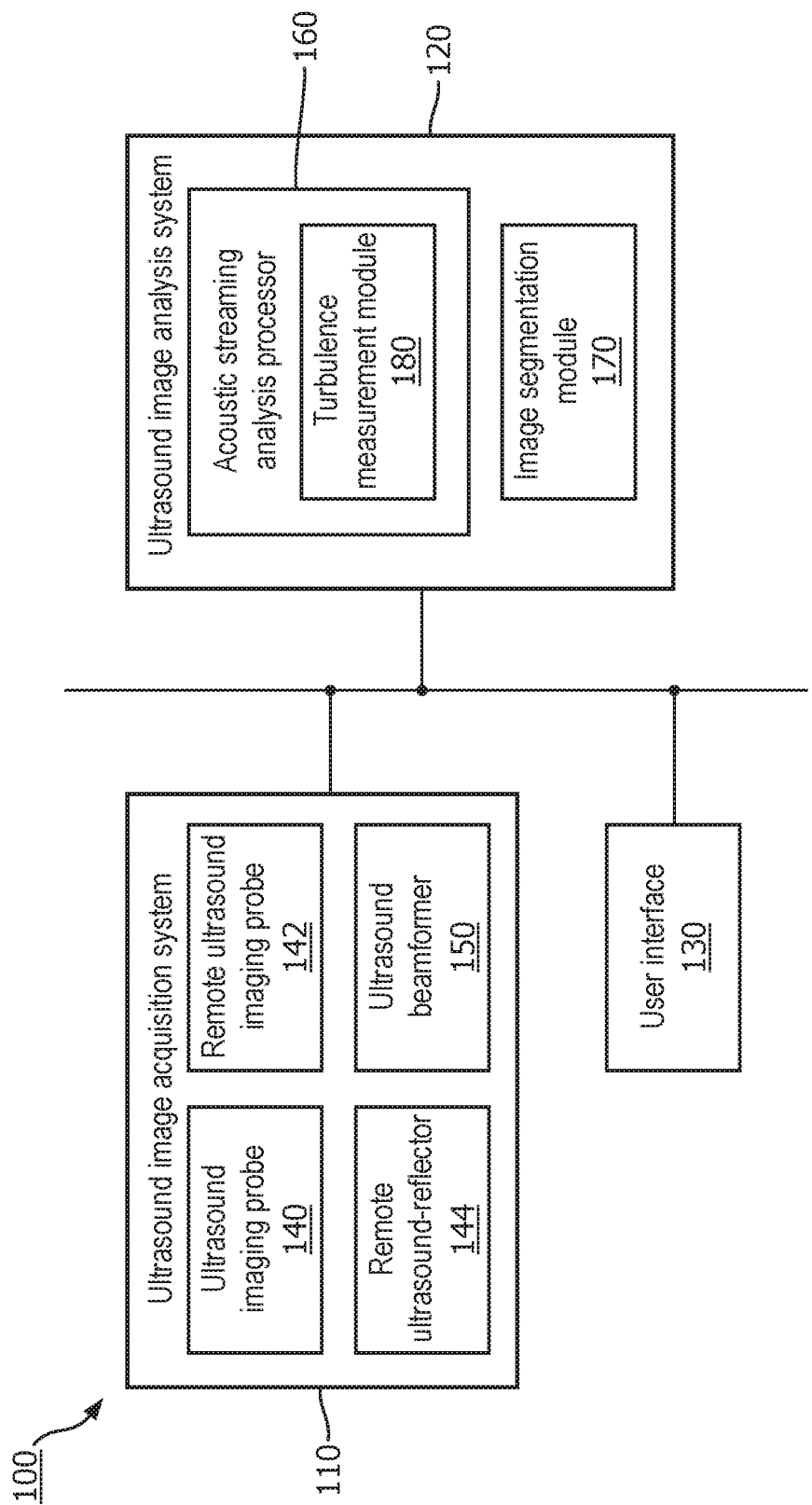
FIG. 1 is a schematic diagram of one example of an acoustic-streaming-based liquid, and blood pool, detection and localization apparatus, in accordance with the present invention.

FIG. 1 depicts, by way of illustrative and non-limitative example, an acoustic-streaming-based liquid, and blood pool, detection and localization apparatus 100. The apparatus 100 includes an ultrasound image acquisition system 110, an ultrasound image analysis system 120, and a user interface 130.

Included in the ultrasound image acquisition system 110 are an ultrasound imaging probe 140, a remote ultrasound imaging probe 142 and/or a remote ultrasound-reflector 144, and an ultrasound beamformer 150. The imaging probe 140 incorporates at least one ultrasound transducer (not shown). The transducer is configured for conventional ultrasound imaging modes, e.g., A-mode, two-dimensional (or "B-mode") imaging, Doppler, contrast imaging, color flow imaging, etc. It is further configured for producing, i.e., forming and emitting, acoustic-radiation-force-based push pulses for acoustic streaming. Alternatively, separate transducers may be provided. For example, one can be designed for generating the push pulses with respective foci. The other can be designed for generating lower-powered tracking pulses along multiple beam directions, and for the B-mode imaging. The two types of transducer may be concentically arranged.

The ultrasound image analysis system 120 includes an acoustic streaming analysis processor 160 and an image segmentation module 170. The acoustic streaming analysis processor 160 in the current example includes a turbulence measurement module 180, although several other additional or alternative solid/liquid discriminating modules could be included as well, as will be clear from the discussion herein below. The ultrasound image analysis system 120 is configured for considering together a result of echogenicity-based body tissue area identifying and a result of post-acoustic-push movement-characteristic detecting in deciding whether a body tissue area is a blood pool. In some embodiments, this decision function is allocated to a fluid pool identification processor (not shown) within the system 120.

Figure 2:
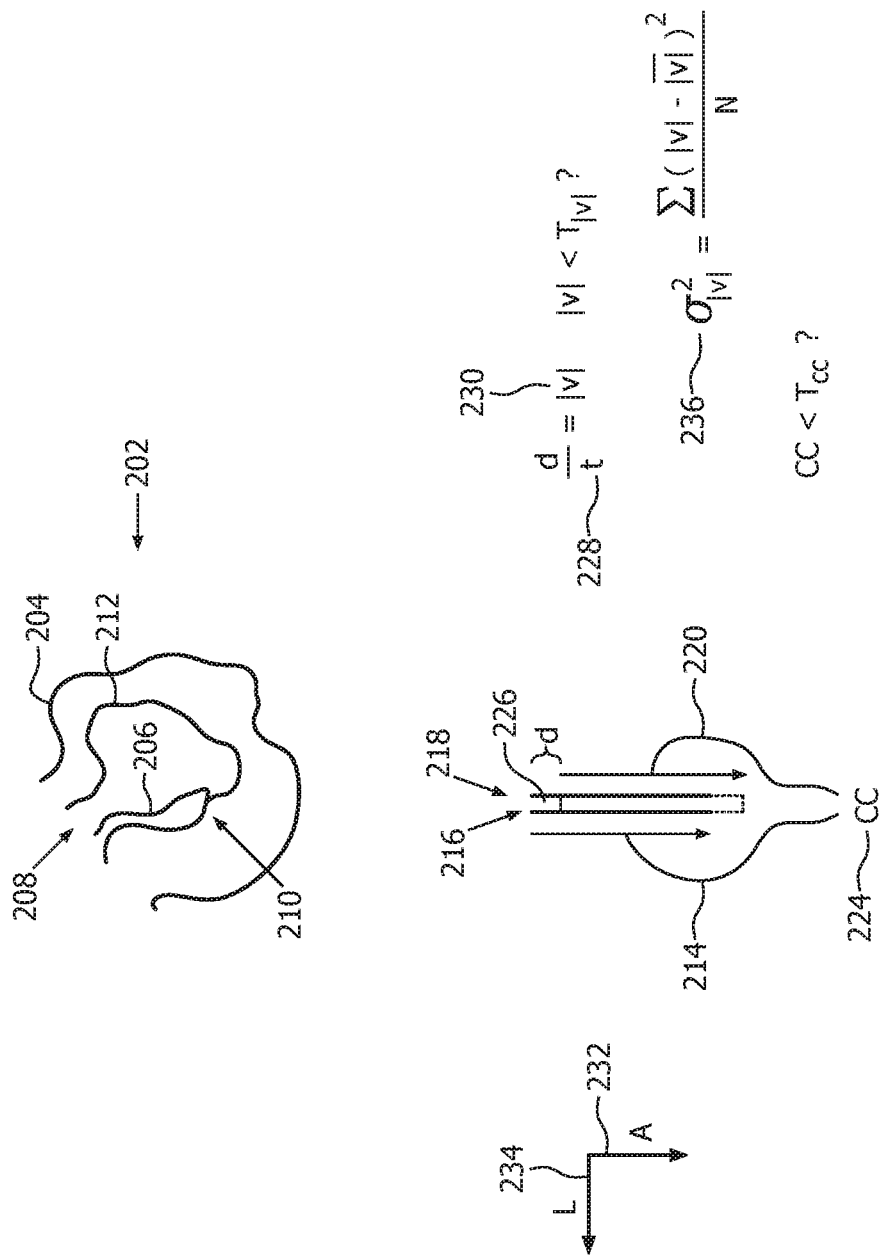
FIG. 2 is a conceptual diagram exemplary of, and pertaining to, the apparatus of FIG. 1.

FIG. 2 introduces some elements or concepts of what is involved in the proposed methodology. An ultrasound B-mode image 202 depicts a cross-section of a portion 204 of an intestine of a patient, human or animal. Also shown is a part of a large blood vessel 206 that, according to the image 202, runs partially alongside the intestinal portion. Both the vessel 206 and the somewhat circular, somewhat closed off region 208 shown in the image 202 inside the intestinal portion are hypoechoic. Here, the hypoechoic (or hypoechoic-appearing) region 208 in the image visible on a two-dimensional display screen is to be distinguished from a three-dimensional hypoechoic area 210 in the body tissue. The hypoechoic area 210 can be automatically identified from image brightness values, as discussed in more detail herein below. However, not all hypoechoic areas 210 are blood pool. While hypoechoic areas 210 are easy for the experienced sonographer to visually identify in B-mode images from among the darkness in the image, not all dark areas necessarily imply blood pool, since other regions such as fat, cysts containing watery fluid perhaps with solid tissue, blood vessels, blood clots, certain tumors, or rib shadows could also appear hypoechoic. Therefore, echogenicity readings alone cannot be relied upon for making an automatic determination. In FIG. 2, the overall, roundish shape of the region 208 is characteristic of blood pool in the intestinal area. This kind of observation as to shape is used to filter the set of candidate area 210, eliminating as candidates those areas not found to meet a specific shape criterion. To verify that the surviving-candidate hypoechoic area 210 is a blood pool, it is proposed to take acoustic streaming readings from the area—in preparation for taking the readings, however, the blood vessel 206 is to be identified. In the actual taking of the acoustic streaming readings, the blood vessel 206 is avoided, since the natural flow of blood in the vessel might be hard to distinguish from acoustic streaming. As discussed further below, a vessel map can, from the outset, be created from the radiofrequency (RF) data, so that the tracking involved in testing can avoid any vessels 206. Thus, the localizing of blood pools takes into account the identification of blood vessels 206.

In the FIG. 2 example, as just mentioned, the roundish border, i.e., shape 212, is a pattern of echogenicity that is automatically detected by virtue of its roundness. This may lead to identification, based on the pattern, of a candidate hypoechoic area 210 in which the material 324 to be tested, for acoustic streaming, is located. An alternative to automatic identification is interactive user indication on the user interface 130. The apparatus 100 might be equipped both with the segmentation module 170 for the automatic identification and with logic for operating the user interface 130 for receiving, from the user, an identification of the candidate hypoechoic area 210. The user identification may be an interactive onscreen identification by any known and suitable means. The apparatus 100 is, due to the automatic identification feature, more easily operated by an inexperienced clinician. The feature also offers convenience for the experienced clinician. Advantageously too, once a candidate region is identified either automatically or by the user, the acoustic streaming verification need only be performed for a single line or merely with a few push pulses to the middle of the detected area, as described in more detail herein below, rather than throughout the whole region. Also, only the candidate regions, three for example, need be further considered. The power overhead is accordingly reduced, leading to the above-discussed benefits.

Blood has poor echogenicity, and a search for blood pool can take into account the local brightness of an ultrasound image.

Automated segmentation of the ultrasound image 202 can be done to determine all dark (i.e., hypoechoic-appearing) regions within the ultrasound image, the determined regions then becoming candidates for being characterizable as blood pool. There exist several methods for ultrasound image segmentation, including: optimal threshold techniques; edge or boundary-based methods; region based segmentation techniques; hybrid techniques combining region and boundary criteria; texture based segmentation; and snakes or active contour.

Many conventional algorithms use a seed point of the region of interest (ROI), typically provided by manual interaction and, in any event, slowing the segmentation.

However, a hybrid combination technique without using a seed point can be used in the segmentation of dark areas of relatively large size (eliminating discrete points possible from speckle noise).

Four major steps are usable in the automated segmentation: pre-processing, multiscale gradient, watershed segmentation or other hybrid techniques, and reconstruction.

As to pre-processing, an ultrasound image usually has, at least at the outset, relatively low contrast and poor quality due to speckle noise. A pre-processing technique such as histogram equalization is done to increase the global contrast of the image by increasing the range of gray levels in the image. This can be followed by median filtering to remove speckle noise and salt-and-pepper noise.

Conventional gradient algorithms often produce too many local minima, and low gradient values at blurred edges, leading to possibly inaccurate segmentation. A solution is to use a multiscale morphological gradient operator that provides better segmentation after removing local minima using morphological methods.

Watershed segmentation divides an image into watersheds. In particular, the pixel by pixel intensities can be analogized to topographically defined terrain, with pixel intensity being indicative of elevation. Water drainage patterns provide the division. The goal is to find a number of watersheds in the image, each watershed corresponding to and spatially defining a candidate hypoechoic area 210. If many candidates have been determined from the steps above, then the area of each candidate could be computed as well. If the area of a candidate is too small compared to other candidates, it is less likely that the candidate is a blood pool. On the other hand, the shape for each candidate could be determined as well. Specific shape features that are, as mentioned above and in the discussion that is to follow, characteristic of blood pool resulting from chest or abdominal trauma could be used to reduce the number of candidates. Alternatively to watershed segmentation algorithms, other hybrid segmentation techniques could be used to achieve similar results.

Alternatively, the hypoechoic areas 210 can be detected and defined by cluster analysis on spatially adjacent pixels of sufficiently low brightness.

The candidate areas 210 are each tested for the presence of particular shapes in the ultrasound image. The shape testing is performable as a next filtering step, as a prelude to acoustic streaming testing. Or, a combined approach can be followed which is disclosed in V. Zagrodsky, et. al. (hereinafter "Zagrodsky"), "Automated detection of a blood pool in ultrasound images of abdominal trauma", Ultrasound in Med. & Biol., 2007, Vol. 33(11): 1720-1726, the entire disclosure of which is incorporated herein by reference.

Zagrodsky discloses an automated method of blood pool detection in the abdominal area.

The Zagrodsky paper observes that a blood pool in an ultrasound image of the abdominal area appears as a hypoechoic area having a sharp angle, and that another typical feature is the presence of bright edges. The latter correspond to outlines of surrounding organs. The brightness contributes, for example, to distinguishing these edges from acoustic shadow, the distinguishing being dependent on the existence of high contrast and sufficiently long edges. The former characteristic of a sharp angle differentiates blood pool residing between organs, such as the liver and a kidney, from regular soft-curved shapes of fluid-filled abdominal organs.

Blood pool appears in the ultrasound image either as a largely rounded closed shape, as seen from the shape 212 in FIG. 2, or it can appear as a stripe, or exhibit a sharp angle. In particular, a very typical shape of blood pool is a stripe in Morrison's pouch, the latter being located between the liver and right kidney. These shapes have a very high contrast to underlying normal soft tissue.

After the above-discussed pre-preocessing, Zagrodsky evaluates regional features, then clusters feature space, and, finally, detects the areas in which all features meet predefined assumptions.

Zagrodsky, as mentioned herein above, detects dark areas, bright edges and sharp angles, in a combined approach.

Gradient magnitudes of local image contrast are used to evaluate edge intensities. Averaging is performed with square tiles of size T. Differences of intensities I are computed for all possible image shifts within the half tile, using the following equations:

$$J_{ij}i = \Sigma_x \Sigma_y (I(x,y) - I(x+i, y+j))$$

where i, j=[−T/2, T/2], x, y=[O, T], and $$G(x, y) = \max |J_{ij}|/(\Sigma\Sigma (I(x, y))^{1/2}$$

The function G, i.e., the normalized averaged gradient magnitude, ignores small features of size less than T, while preserving only the elements having sufficiently high contrast. A tile size of 16×16 or 32×32 may be used. The direction orthogonal to the detected edge is provided by the indices i an j when $|J_{ij}|$ achieves its maximum.

Quantitative metrics of local shapes are determined using central rotation invariant Hu moments (Hu 1962; Prokop and Reeves 1992). Hu moments of the second order are applied to distinguish blood pools from fluid-filled abdominal organs, based on the above mentioned respective difference between sharp angles and the regular soft-curved shapes. The two second-order moments are:

$$M1 = n_{20} + n_{02}$$

$$M2 = (n_{20} - n_{02})^2 + 4n_{11}^2$$

where $n_{pq} = m_{pq}/m_{00}^2$ (for p+q=2) are the normalized central moments, $m_{pq} = \Sigma_x \Sigma_y (x-x_0)^p (y-y_0)^q I(x,y)$ are the regular central moments, $\xi_0 = \Sigma_x \Sigma_y x I(x,y)/m_{00}$ are the coordinates of center of mass, and the zero-order moment $m_{00} = \xi_x \xi_y I(x,y)$ is a sum of intensities I in a current image tile x, y=[0,T].

Areas where the three extracted features match are found by the algorithm. These areas consist of pixels in which all three of the individual metrics (i.e., intensity I, normalized averaged gradient G, and the ratio of second-order Hu moments M) meet certain predefined criteria.

A round kernel, e.g., 15-pixel or within the 13-16 range, is used in gray-level dilating of the three feature images, in which maximal feature values of interest, such as the gradient and the ratio of moments, are expanded. Dilation is applied to the negative of the image, so as to expand minimal values.

A three-dimensional feature space is formed from the three resultant individual metrics such that every pixel is mapped to a point having coordinates equal to its metric values. In the feature space, fuzzy k-means clustering is performed. The original pixels are then highlighted by mapping back the points belonging to selected clusters. Using predetermined selection thresholds, a cluster is selected if its significant part resides in the appropriate corner of the feature space.

The hypoechoic regions 210 identified are then subject to acoustic streaming testing and, optionally, the further tests seen herein below in FIG. 7.

An alternative example of an automated method for identifying a rounded shape is as follows. Find the centroid, i.e., the arithmetic mean of both Cartesian coordinates, of the hypoechoic region 208. Find the circle, centered at the centroid, with the same area as the hypoechoic region 208. Going around the circumference, at each point find the distance of the normal to the boundary of the region 208. Sum the absolute values of the distances. Normalize the sum to the radius. Compare the normalized sum to a roundness threshold.

As mentioned herein above, blood pool near the intestinal coils tends to have a round or near round shape, and the above-described rounded shape identifying can be used.

Also, since simple cysts have regular circular geometry, the above-described rounded shape identifying is usable for identifying a simple cyst, by utilizing a relatively strict roundness threshold.

An alternative example of an automated method for identifying a stripe is as follows. Find the centroid. Rotate a line about the centroid and across the image to find an orientation of minimal total absolute distance from image pixels to the line. Compare the minimum distance to meet a straightness threshold, with some predetermined amount of curving of the stripe being tolerated.

Returning to FIG. 2, the wall of the intestinal portion 204 is a region adjoining the hypoechoic area 210. The wall can therefore used in testing for the existence of acoustic streaming caused by the application of acoustic power. In particular, a series of one or more push pulses can be emitted both to a central location within the candidate hypoechoic area 210 and to the adjoining soft tissue, i.e., wall of the intestinal portion 204. Relative resulting motion in the area 210 with respect to the soft tissue is observed. If, in particular and by way of example, it is detected, by the tracking pulse or pulses issued following the push pulse(s), that the ratio of motion meets an acoustic streaming detection threshold, the entire hypoechoic area 210 is deemed to be blood pool.

Another way of detecting acoustic streaming is to detect sufficient decorrelation of body tissue being displaced in relation to an earlier position of the tissue. Even if the applied acoustic power significantly moves solid tissue, the tissue tends to sufficiently retain its form for cross-correlation and to elastically return to its original position. Liquid tissue, by contrast, continues its displacement in the direction of applied acoustic force, progressively deforming turbulently.

Referring again to FIG. 2, a kernel 214 of one A-line 216 exhibits maximum cross-correlation with a second, spatially coincident, and temporally subsequent, A-line 218 by matching a section 220 of the second A-line. The greater the time interval between the two A-lines 216, 218, the lower the maximum correlation coefficient 224. Thus, given a sufficient time interval, the correlation coefficient 224 can effectively be compared to a correlation coefficient threshold $T_{CC}$. If it is below the threshold $T_{CC}$, the displaced tissue is determined to be liquid. The time interval will be sufficient if the tracking pulse is sufficiently delayed or is a sufficiently later tracking pulse in a series of tracking pulses. The correlation coefficient 224 is based on images acquired, via the image acquisition system 110, with an intervening delay for decorrelating the images, in case of acoustic streaming, due to the acoustic streaming.

Tissue displacement 226 that corresponds to the distance d yields the maximum cross-correlation, and the displacement d occurs over a time period t 228. Thus, the displacement 226 occurs with a speed of $|v|$ which is equal to d/t. Here, the flow speed 230 is in the axial direction 232, although acoustic streaming is also characterized by flow speed in the lateral direction 234. The speed 230 in either direction 232, 234 or both may be compared, sampling depth by sampling depth and lateral location by lateral location to one or more respective thresholds $T_{|v|}$. Acoustic streaming, if it exists, may thereby be localized. Alternatively or in addition, variance 236 of the axial and/or lateral flow speed 230 may likewise be assessed over a spatial matrix. Exemplary versions of these latter techniques are discussed in more detail further below.

Figure 3:
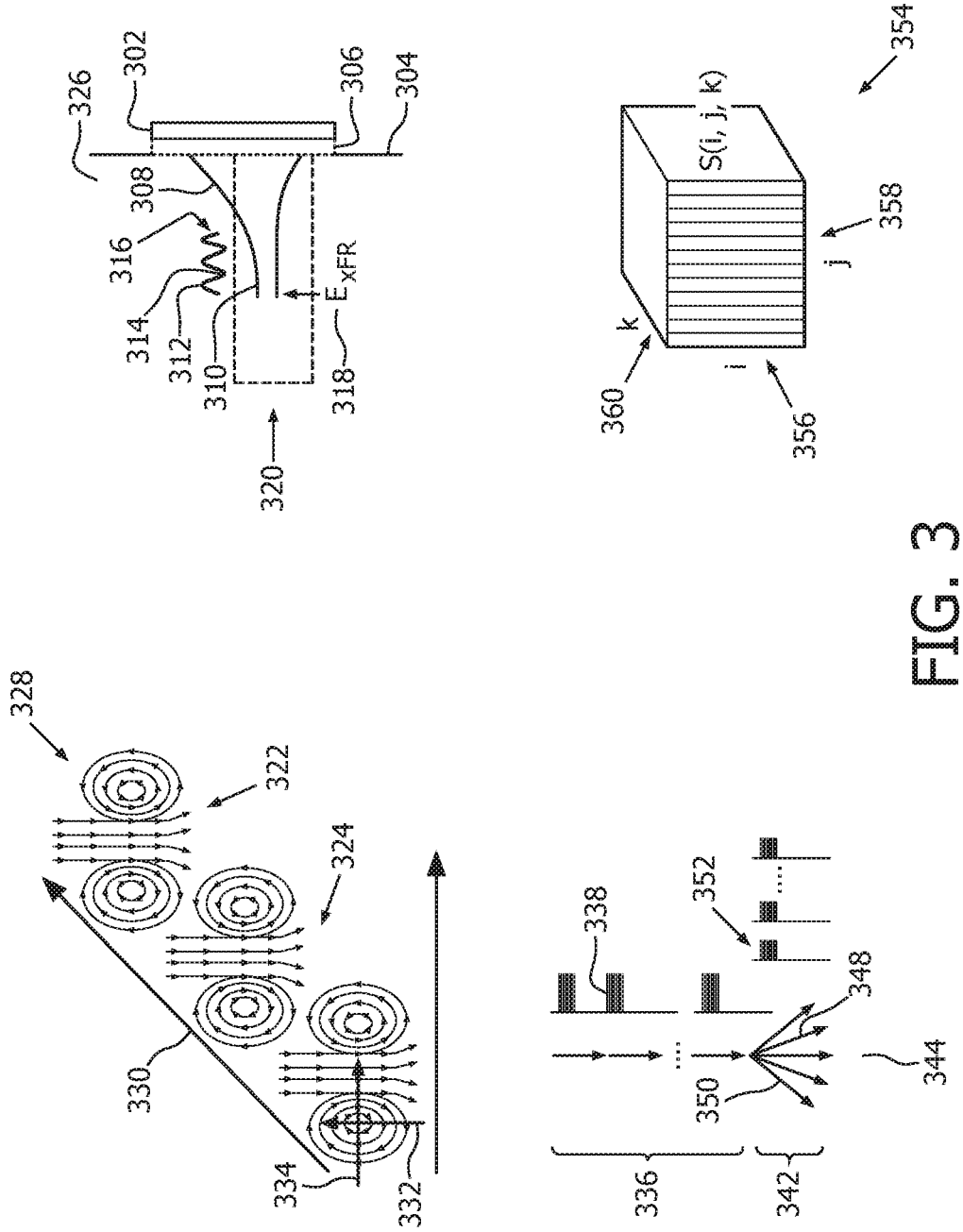
FIG. 3 is a conceptual diagram relating to possible pulsing, in accordance with the present invention.

FIG. 3, like FIG. 2, introduces concepts used in what is proposed herein. A one-dimensional medical ultrasound phased array, which alternatively may be a matrix array, 302 is placed against the skin line 304, separated therefrom by an acoustic gel 306. The array 302, which is part of the probe 140, emits a beam 308 to a focus 310. The beam 308 propagates with alternating compression 312 and rarefaction 314, as an acoustic wave 316. Transfer of energy 318 from the wave 316 creates a sound field 320. The acoustic wave 316 causes, in the sound field 320, bulk movement 322 of material 324, if the material is fluid such as liquid, e.g., blood. The material 324 is in an ultrasound medium 326 such as body tissue of a human or animal. Prior to acoustic stream testing, it is not known whether the material 324 is fluid. The beam 308 is pulsed, resulting in pulsed acoustic power. The material 324 is subjected to the pulsed acoustic power in order to test for the resulting existence of acoustic streaming. The acoustic power induces, in the fluid 324 flow speeds 230 that vary spatially 328 (as represented in FIG. 3 by lines of consecutive arrows) and temporally (as represented conceptually in FIG. 3 along a diagonal axis 330). The spatial variance 236 is axial 332 and lateral 334.

An acoustic radiation force push sequence 336 is emitted to create turbulence, i.e., spatio-temporal variation in flow speeds 230 of the liquid 324 in the sound field 320. The push sequence 336 is a series of 16 push pulses 338 in the same direction. There are between 16 and 32 cycles per push pulse 338, each cycle corresponding to a compression 312 and temporally adjacent rarefaction 314.

The push sequence 336 is immediately followed by a narrowband tracking sequence 342. The signal might be, for instance, 4% or less of center frequency. The tracking region of interest (ROI) 344 can extend from between −10 to 10 degrees or less, with a predefined number of directions 348. In each direction 348, 8 tracking pulses 350 are emitted with 8 cycles per pulse. Thus, not all of the tracking pulses are emitted in the same direction. The tracking pulse 350 is configured with 8 cycles to limit the transmit bandwidth. The 8 repetitions 352 per pulse 350 provide enough acquired data samples for velocity and variance estimation. The ultrasound RF signal is sampled at 24 MHz or higher on each tracking line 216.

Although pulsed acoustic power on the push is used in this example, continuous acoustic power, i.e., one long continuous wave (CW) push pulse, before tracking is an alternative.

The collected ultrasound signal is representable in a three-dimensional (3D) matrix format 354. The three dimensions are imaging depth 356, direction number 358, and repetition number 360.

The first 16 pulses 350 are used to push the fluid pool to create acoustic streaming. Each pulse 350 is made up of 16 full cycles at the center frequency of the transducer 302.

Immediately after the push sequence 336, the tracking sequence 342 is fired. There is accordingly no overlapping between push pulses 338 and tracking pulses 350. The tracking sequence 342 fires 8 pulses 350 in the first direction 348, then 8 pulses in the second direction, et cetera, until all N directions have been interrogated.

A Hilbert transform (or, alternatively, quadrature demodulation) is applied to the received ultrasound RF signal $S(i,j,k)$, with $I(i,j,k)$ and $Q(i,j,k)$ being the imaginary and real part of the result, and with imaging depth 356, direction number 358, and repetition number 360 being respectively denoted by the indices i, j and k. Thus, $$\text{hilbert\_transform}(S(i,j,k)) = Q(i,j,k) + I(i,j,k)\sqrt{-1} \quad (1)$$

The RF data stored in the 3D matrix format 354 constitutes an image. The image is one that includes the material 324 subjected to acoustic streaming testing and is operated upon by the turbulence measurement module 180 of the acoustic streaming analysis processor 160.

1. Velocity Estimation:

The spatial velocity in the axis direction can be estimated using the following equation:

$$V(i,j) = -\frac{cf_{prf}}{4\pi f_0}\arctan\left(\frac{\sum_{k=1}^{7} I(i,j,k+1)Q(i,j,k) - Q(i,j,k+1)I(i,j,k)}{\sum_{k=1}^{7} Q(i,j,k+1)I(i,j,k) + I(i,j,k+1)Q(i,j,k)}\right) \quad (2)$$

where c is the speed of sound, $f_{prf}$ is the pulse repetition rate in Hz, and $f_0$ is the transmit center frequency. The sign of $V(i,j)$ indicates direction. A positive value signifies away from the transducer 302, and negative means towards the transducer.

2. Temporal Velocity Variance Estimation Using IQ Signal Autocorrelation:

The fluid velocity variance in the temporal (i.e., k) direction is calculated by the following equation, R being defined as the autocorrelation of $S(i,j,k)$:

$$\sigma_v \cong \frac{cf_{prf}}{2\sqrt{2}\pi f_0}\sqrt{1 - \frac{|R|}{\text{Power}(S)}} \quad (3)$$

Where $\sigma_v$ is velocity variance, $|R|$ is the absolute value of the receive signal's autocorrelation function in complex format, and Power (S) is the receive signal's power. The lag 0 autocorrelation of $S(i,j,k)$ is $\Sigma_{m=0}^{7}(S(i,j,m)*S\dagger(i,j,m))$, where $S\dagger$ denotes the complex conjugate of S.

3. Temporal Velocity Variance Estimation Using RF Tracking:

Rather than the velocity estimation using the phase auto correlation in (2), the fluid's velocity can also be estimated by an RF tracking method. The RF tracking method uses the cross-correlation between the two adjacent ultrasound frames for the ROI 344 and finds the highest correlation coefficient. The shift of the ROI, $\Delta d$, represents the displacement of the particle reflecting the ultrasound field. The particle's velocity can be calculated using $v = \Delta d/\Delta t$.

Since there are eight tracking lines, this will result in seven velocity estimations corresponding to different time stamps. The standard deviation of the velocity is an indicator of the velocity variance.

4. Spatial Velocity Variance

The fluid streaming velocity 230 incurred by the acoustic pushing will also vary spatially, i.e., laterally 234 and axially 232. For example, an indicator of the variation in the lateral direction 234 can reflect variation, at a given imaging depth, of velocities at that depth for a series of adjacent lines. The velocity direction varies line by line. The standard deviation of these speeds can serve as the indicator.

For each of numbers 1 through 4 above, velocity/velocity variation maps can be formed of different functions of imaging depth and lateral position. As mentioned herein above, ultrasound interrogation is confinable to merely a single line 348 to determine whether the current candidate hypoechoic area 210, having a targeted specific shape, is in fact a blood pool. Moreover, only a few push pulses 350 are applied to induce acoustic streaming that will be subject to that interrogation. However, the velocity/velocity variation maps can go beyond the testing of a single line 348, and the push sequence 336 can go beyond merely a few push pulses, making the methodology more robust. Accordingly, repetition of the push and tracking sequences 336, 342 can be performed throughout the current FAST view. Alternatively, the preparatory identification of the hypoechoic areas 210 can be foregone, relying on just such a repetition, although the vessel map will still be formed initially to avoid acoustic streaming sampling in a blood vessel 206.

With regard to the velocity/velocity variation maps and by way of example, a velocity map can be estimated from autocorrelation using equation (2). Velocity values in the map serve as indicators such that higher velocities evident from the map will identify and define the spatial extent of a blood pool.

A standard deviation, imaging depth by imaging depth, can be derived from the velocity map, i.e., from the velocities in the lateral direction, thereby yielding standard deviations, as indicators, per each imaging depth. The higher standard deviations likewise identify and define a spatial extent of a blood pool.

Alternatively or in addition, a temporal velocity variance map, likewise functionally based on imaging depth and lateral position, can be estimated from equation (3). Here too, standard deviations serve as indicators, and higher-valued ones identify and define the spatial extent of a blood pool. The center line of the temporal velocity variance map, running in the imaging depth direction, is usable to identify and define a spatial extent of a blood pool.

Figure 4:
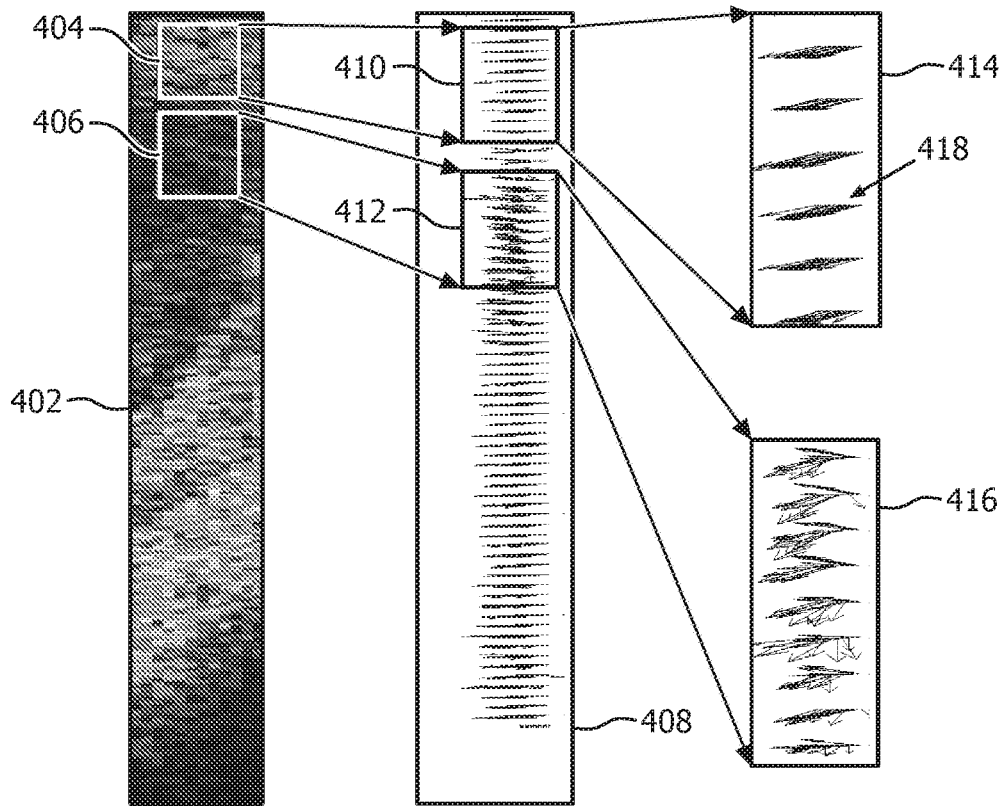
FIG. 4 is a conceptual diagram an acoustic streaming detection criterion, in accordance with the present invention.
Figure 4:
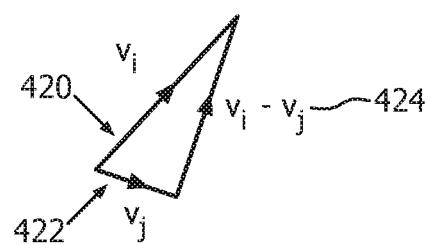

In another version of turbulence measurement, a more detailed velocity distribution can be estimated based on two-dimensional speckle tracking. Referring to FIG. 4, a B-mode image 402 is shown for purposes of illustration. Two square-shaped sections 404, 406 of the image 402 are, again for purposes of illustration, analyzed in a velocity vector map 408. The corresponding two square-shaped sections 410, 412 of the velocity vector map 408 are expanded, as by a zooming function, for illustration as two zoomed boxes 414, 416. In the first 414 of the boxes, six groups of velocity vectors are shown. Each group 418 consists of velocity vectors of flow measured at a particular imaging depth. Since two-dimensional speckle tracking has been used here, each vector has a two-dimensional direction. For simplicity of illustration, the two orthogonal directions for the vectors have been reversed, so that the axial direction is horizontal across the page, and the lateral direction is vertical. Visually comparing the two zoomed boxes 414, 416, it is seen that, in one of the boxes, box 414, the velocity vectors are more uniform than in the other of the two boxes, box 416, where they are more random. This is because box 414 is showing velocity vectors from a region of solid tissue, whereas box 416 is showing velocity vectors from a region of fluid. An algorithm for measuring randomness is as follows: for all pairs of vectors $v_i, v_j$ in the set, join the two upstream ends 420, 422, and calculate the absolute value of the vector difference $v_i - v_j$ 424; average the absolute values; divide the average by the average of the magnitudes of the original vectors to yield a normalized vector randomness measure 426; do this on a sliding window basis by imaging depth; and compare the measures 426 to a randomness threshold $T_R$ 428 to identify and determine a spatial extent of fluid regions. The above methods can be extended to three orthogonal dimensions, by using 3D ultrasound. Unique features derived from 3D velocity, such as turbulence and vortex, are usable to distinguish fluid from solid tissue.

As discussed herein above, acoustic streaming detection can be effected by measuring decorrelation encountered in speckle tracking. FIGS. 5A-5D and 6A-6D relate to observing tissue displacement periodically, i.e., imaging frame by imaging frame, after a push, such as a series of a few push pulses. This is shown in FIGS. 5A-5D and 6A-6D for a series of 10 frames.

Figure 5A:
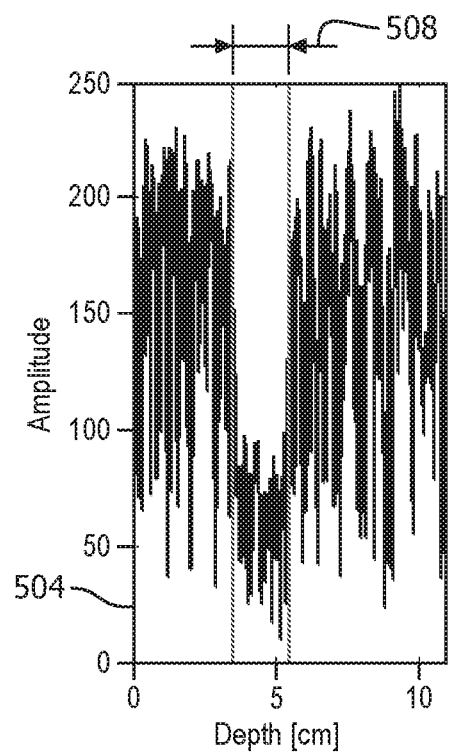
FIGS. 5A-5D and 6A-6D are conceptual diagrams of another acoustic streaming detection criterion, in accordance with the present invention.
Figure 5B:
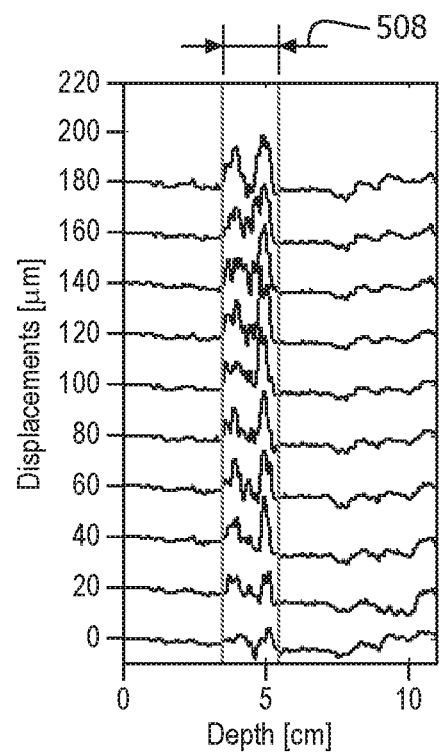
Figure 5C:
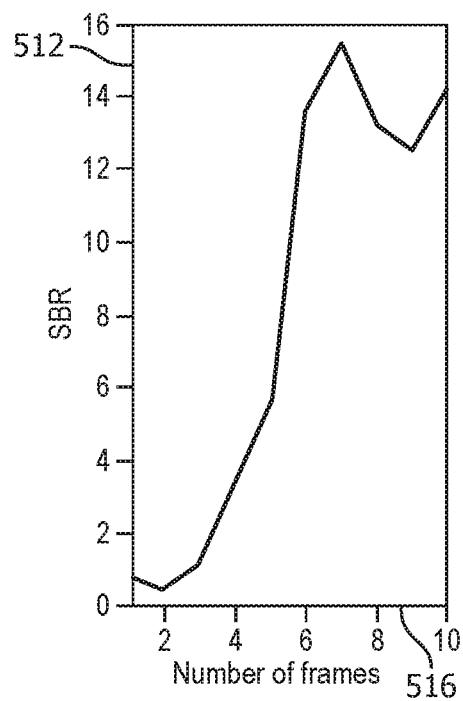
Figure 5D:
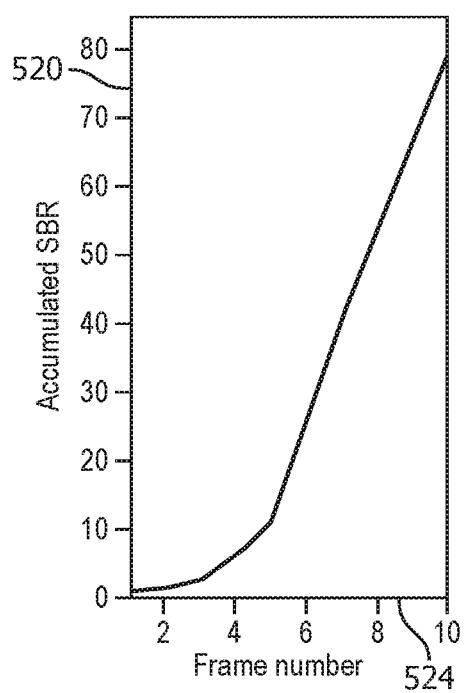

As to FIG. 5A, the amplitude axis represents echo intensity 504. The intensity 504 falls off in an imaging depth range 508 indicated in FIG. 5A by two vertical lines as being approximately between 3.5 and 5.5 cm. Blood pool resides in this range 508, and its relatively lower echogenicity is exhibited by the fall off. FIG. 5B shows, for the same imaging depth range 508, markedly greater displacement than outside the range. The 10 graphs in FIG. 5B correspond respectively to the data acquired in the first 10 of a sequence of 20 imaging frames. The graphs are depicted spaced apart from each other, since their superimposition would obscure each individually. Each imaging frame contains data from various lateral locations, and the graph for each frame represents displacement observed from a middle A-line. For FIGS. 5A and 5B, outside the range 508 can be considered "background", and inside the range can be considered "signal." Thus, the amount of displacement observed in frame x+1 beyond the displacement observed in frame x is the signal. A value corresponding to a comparison between signal to background, i.e., a signal to background ratio 512, is the vertical axis of the graph in FIG. 5C. The ratio 512 is averaged over a number 516 of frames, or "time periods." An accumulated signal represents the displacement accumulated since frame 1. FIG. 5D shows an accumulated signal to background ratio 520, repeatedly plotted as a function of the number of frames 524 over which the accumulating has taken place. After an initial curve before frame 5, the slope is straight, or constant, at about 15.

Figure 6A:
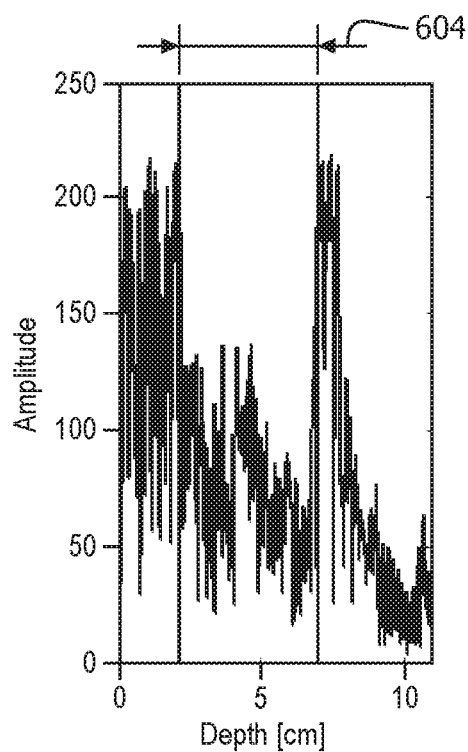
Figure 6B:
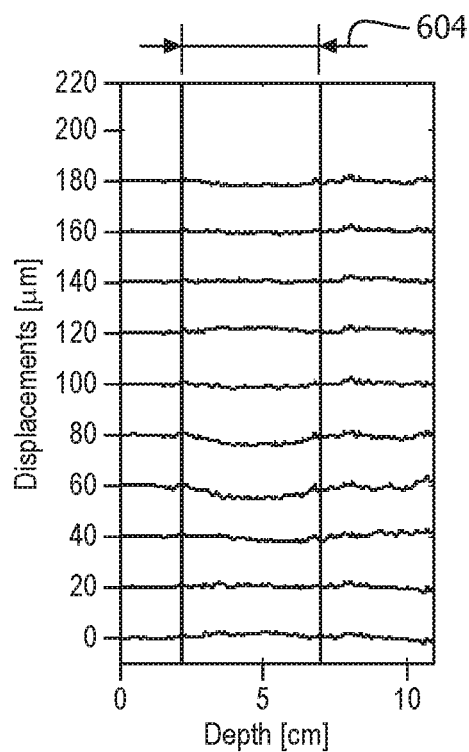
Figure 6C:
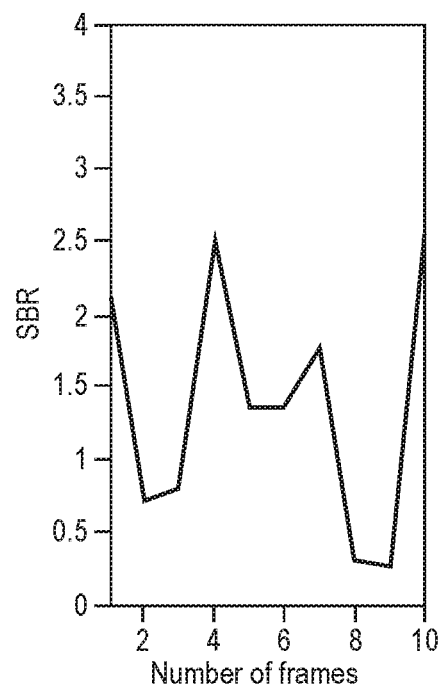
Figure 6D:
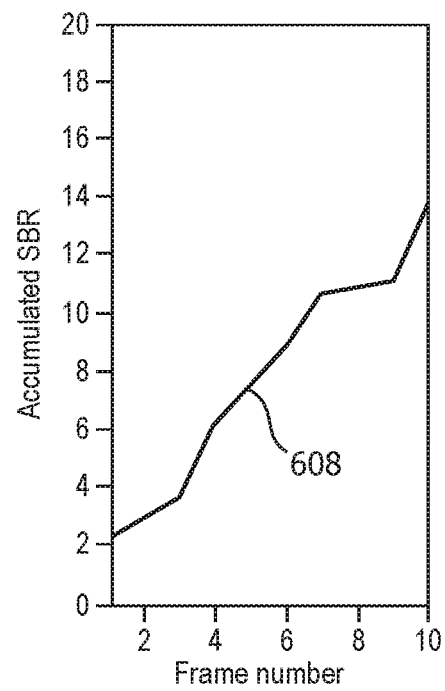

Referring to FIGS. 6A-6D for comparison to FIGS. 5A-5D, an imaging depth range 604, as shown in FIG. 6A, is characterized by a markedly lower echo intensity. This might be the case if the tissue within the range 604 is a blood clot or fat, for example, which can be largely hypoechoic but is not blood pool. It is seen from FIG. 6B, that the imaging depth range 604 exhibits little displacement, as is characteristic of a region of solid body tissue, such as fat or a clot. For the solid body tissue, the accumulated signal to background ratio graph 608 in FIG. 6D does not have a straight slope after an initial number of frames, and the slope of about 1.3 is distinguishably less than the slope of about 15 in FIG. 5D for blood pool. Accordingly, an automated decision can be made, based on at least one of straightness, and slope, of the graph 608, whether material within the range 604 is liquid.

Figure 7:
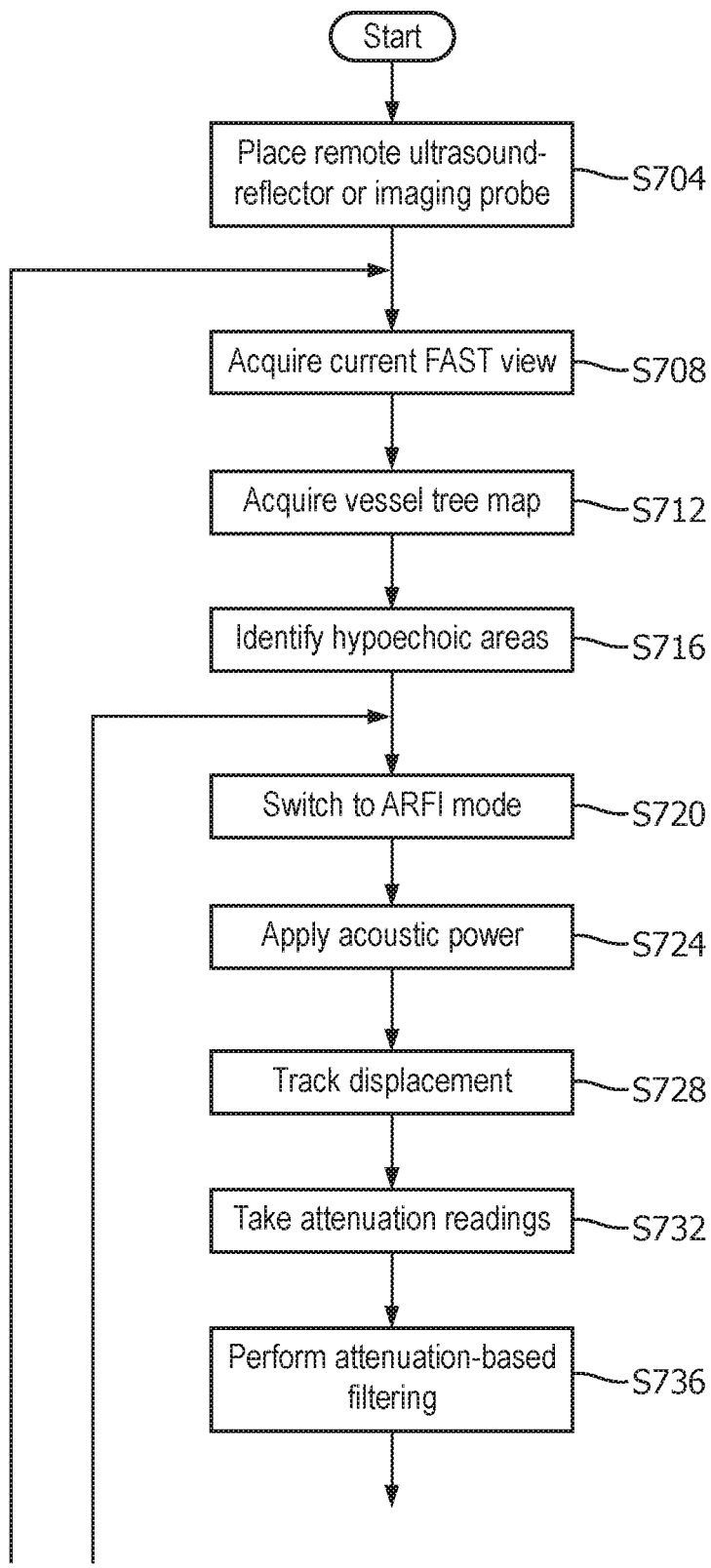
FIGS. 7 and 8 are flow charts illustrative and exemplary of operation according with the present invention.
Figure 7:
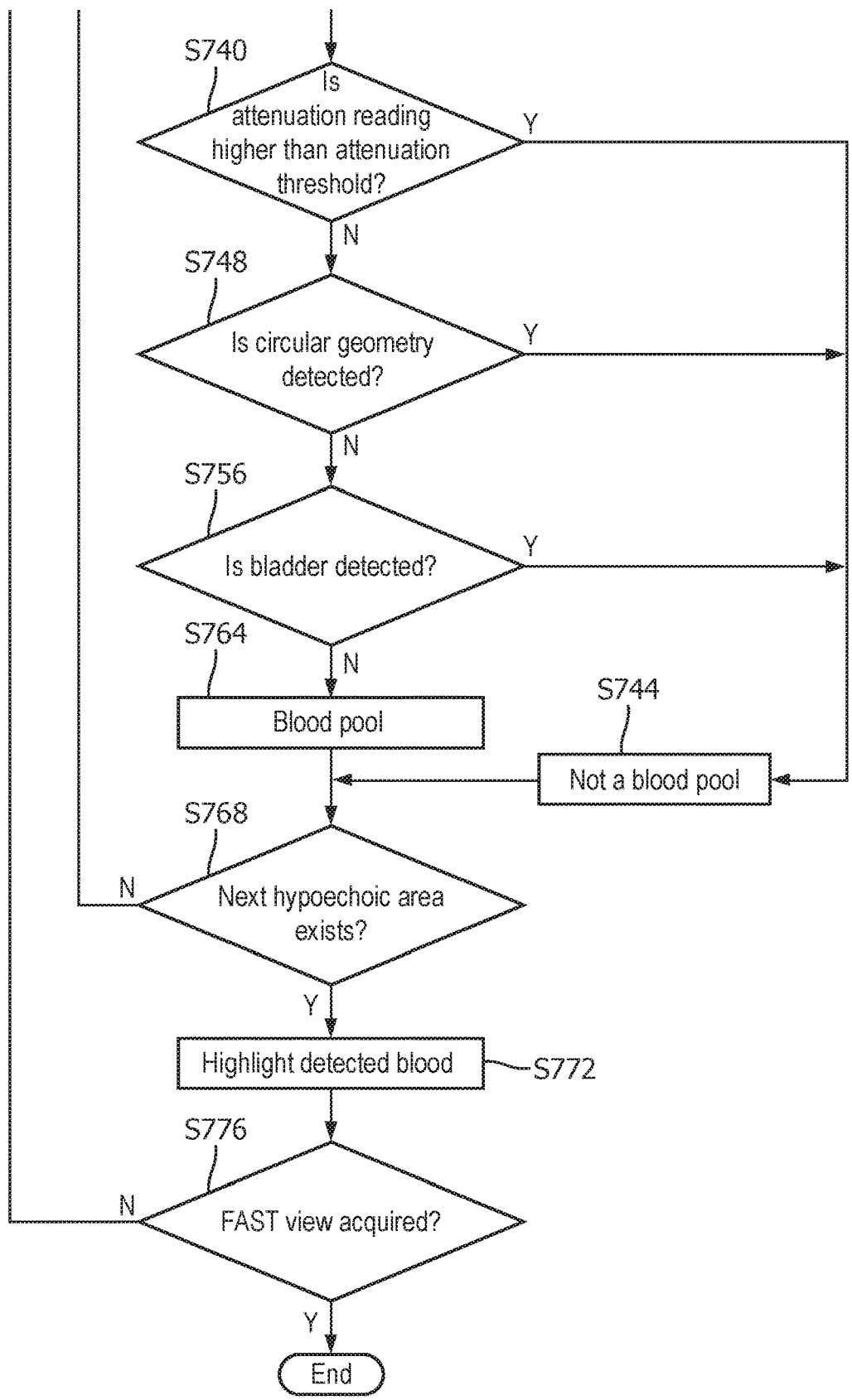
Figure 8:
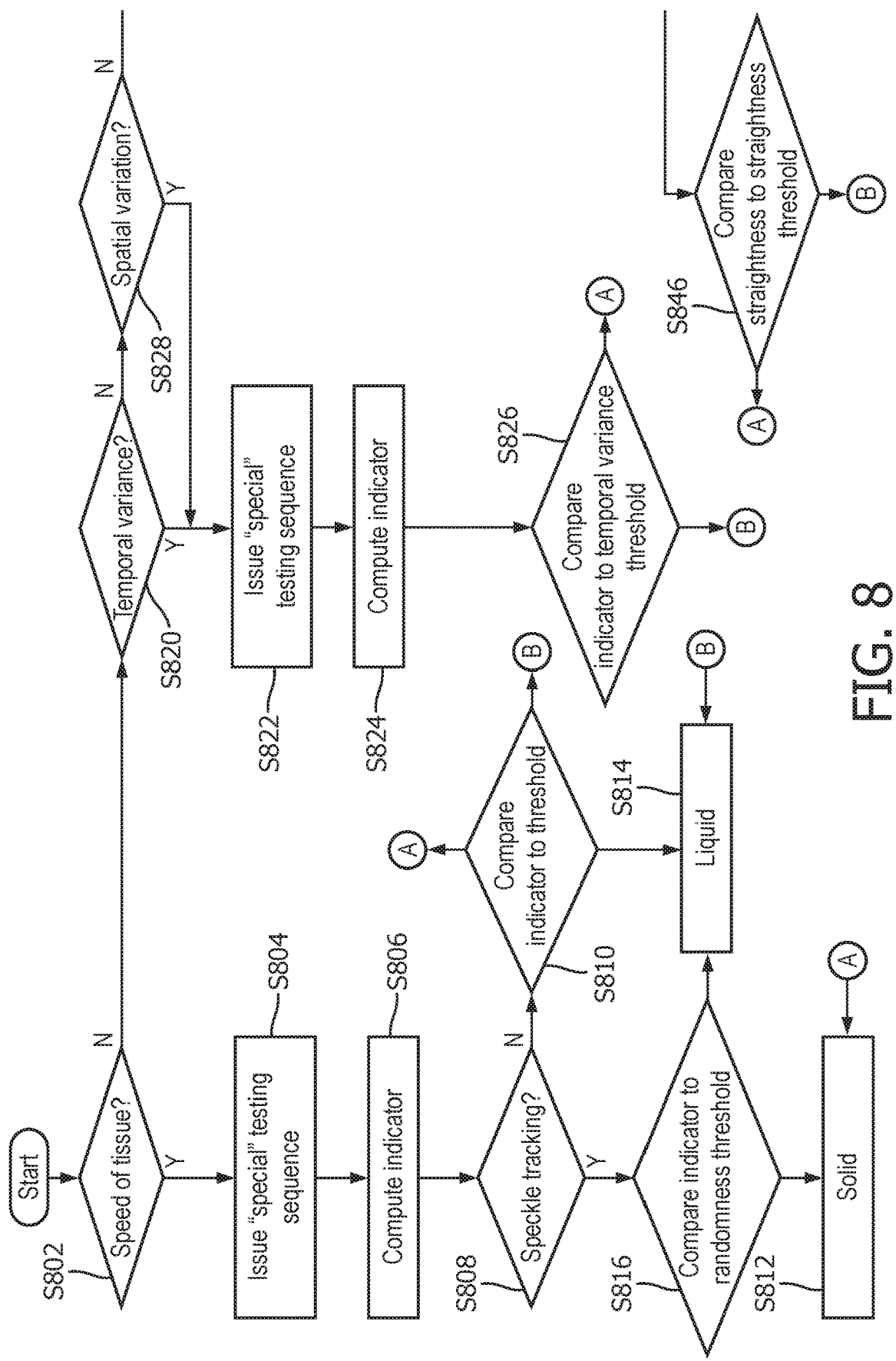
Figure 8:
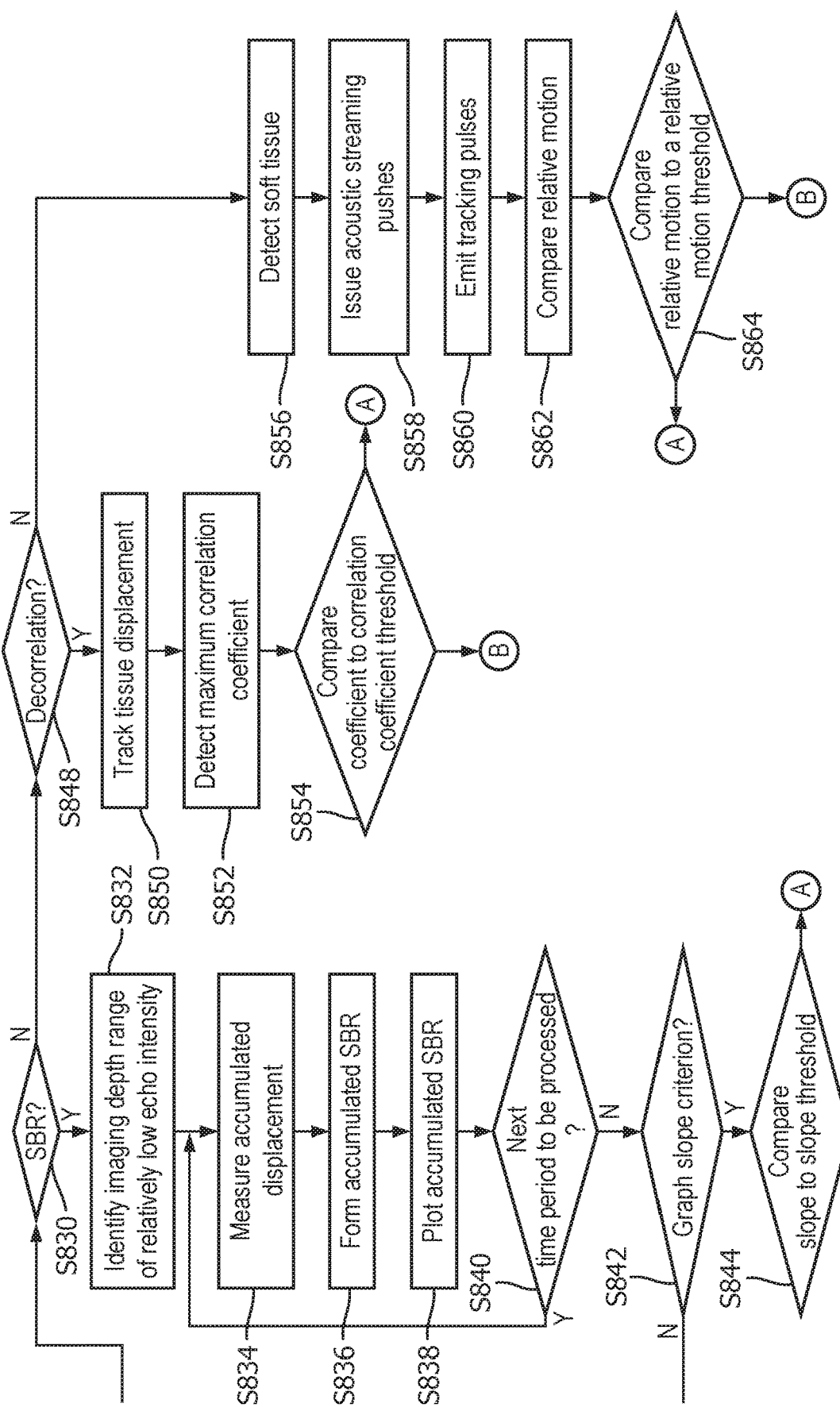

FIGS. 7 and 8 present steps in carrying out the proposed technology and an embodiment that uses detected attenuation in body tissue in identifying a blood pool.

Referring to FIG. 7, in an attenuation detection embodiment a remote ultrasound-reflector 144 is placed underneath the trauma patient who is in the supine position, although the remote ultrasound imaging probe 142 may instead be placed (step S704). The reflector 144 or probe 142 are flat, and are wide enough to span the torso of the patient. The use of either device 142, 144 to automatically obtain attenuation readings is well-known, as described in U.S. Patent Publication No. 2006/0116579 to Li et al. (hereinafter "Li"), the entire disclosure of which is incorporated by reference. More details on signal processing, and signal processing refinements, in automatically acquiring ultrasound RF data and automatically deriving attenuation readings from the acquired data are provided in U.S. Patent Publication No. 2013/0079641 to Zwirn, the entire disclosure of which is also incorporated by reference. As in Li, a B-mode image will be acquired to improve estimation accuracy, although this, and the attenuation estimation step as a whole, are deferred until the hypoechoic areas 210 are determined, later in step S732. The operator applies the (non-remote) imaging probe 140 to acquire a current FAST view (step S708). As a preparatory step with the imaging probe in place, a vessel tree map, for the current view, is acquired via B-mode imaging, Doppler spectral analysis, or color flow imaging (step S712). Doppler spectral analysis provides an automated way of extracting the vessel tree map. Doppler color flow imaging is an alternative which provides less spatial resolution. In addition, a B-mode image is used to identify the hypoechoic areas 210 (step S716). This may occur via the segmentation discussed herein above. In particular and as discussed herein above, based on echogenicity evidenced in an ultrasound image of material 324 subjected to an acoustic wave, a body tissue area depicted in the image is identified and localized. A characteristic of movement occurring in a body tissue area, such as a characteristic of fluid flow, e.g., turbulence, may now be detected in the current candidate hypoechoic area 210. For such detection, the operator may now switch to acoustic radiation force imaging (ARFI) mode, or the switch may be automatic (step S720). Upon operator actuation, or automatically, acoustic power is applied to create acoustic streaming, although the power, and subsequent tracking, are directed so as to avoid vessels in the vessel map (step S724). An automatic switch is immediately made to regular imaging mode to track displacement caused by the push pulses just emitted (step S728). As mentioned herein above, the tracking results will distinguish solid from fluid tissue and will be used to eliminate acoustic shadows as candidates for blood pool. Steps S724 and S728 are described in more detail in FIG. 8. The above-mentioned attenuation readings, improved by a B-mode image, can now be taken in the hypoechoic areas 210 (step S732). Attenuation-based filtering of the candidate hypoechoic areas 210 is performed (step S736). Solid-type regions include fat, clot, complicated cysts, and tumors provide relatively high attenuation of ultrasound. Certain soft bodily organs are not bright enough in an ultrasound image to be identified as other than blood pool, but provide relatively high attenuation. If the attenuation readings taken in step S732 are higher than an attenuation threshold $T_A$ (step S740), the current candidate hypoechoic area 210 is determined not to be a blood pool (step S744). On the other hand, if the readings do not exceed the attenuation threshold $T_A$ (step S740), further filtration is performed (step S748). For example, if by one of the above-mentioned techniques, a circular geometry has been detected (step S748), a simple cyst is determined to have been found and the current candidate hypoechoic area 210 is determined not to be a blood pool (step S744). On the other hand, if a circular geometry is not found (step S748), bladder detection is performed (step S756). The bladder is automatically detectable by ultrasound harmonic imaging, which mode can be entered automatically. An example of such detection is provided in U.S. Patent Publication No. 2009/0062644 to McMorrow et al. (hereinafter "McMorrow"), the entire disclosure of which is incorporated herein by reference. As seen in paragraph [0061] of McMorrow, an ultrasound image of material 324, i.e., body tissue, is acquired. In what is proposed herein, that tissue would include material 324 that has been subjected to an acoustic wave. The results of the attenuation testing are usable in identifying and localizing a body tissue area depicted in the image. If the current candidate hypoechoic area 210 is found to be bladder tissue (step S756), the current candidate hypoechoic area 210 is determined not to be a blood pool (step S744). Otherwise, if it is not bladder tissue (step S756), the current candidate hypoechoic area 210 is blood pool (step S764). If a next candidate hypoechoic area 210 exists (step S768), return is made to the ARFI application step S720 to process that next candidate hypoechoic area 210. If no next candidate hypoechoic area 210 exists (step S768), the detected blood pool(s) are highlighted in red either as an overlay to the currently displayed B-mode image or as a side-by-side display (step S772). If a FAST view remains to be acquired (step S776), processing branches back to the FAST view acquisition step S708 to acquire that next FAST view. Optionally, processing may also automatically branch back to step S708 to reacquire the "same" FAST view at, for instance, an electronically steered slightly different perspective to verify a determination that blood pool exists. The entire procedure may be configured to, starting at the FAST view acquisition step S708 and for processing of that view, execute automatically, without the need for user intervention. Thus, for example, the decision on whether a candidate hypoechoic area 210 is a blood pool is dynamically responsive to the push sequence 336 and even to the preceding steps, such as acquiring the FAST view and the vessel map. Alternatively, a probe maneuvered by a robotic arm can be programmed to carry out a FAST examination of a motionless, e.g., unconscious, patient, thereby making the entire procedure, after initial probe/reflector placement automated, without the need for user intervention.

As mentioned herein above, the acoustic streaming testing steps S724 and S728 are now described, for various exemplary embodiments, in more detail in conjunction with FIG. 8. If speed of tissue displacement is the current testing technique (step S802), a "special" testing sequence of repeated push pulses 338, followed non-interleavingly with a plurality of tracking pulses 350, is issued (step S804). This special testing sequence is referred to herein above as the push and tracking sequences 336, 342. The special sequence s may be produced over one or two lateral directions 232, 234. The apparatus 100 causes the ultrasound image acquisition system 110, in directing the focus 310 of the pushing acoustic wave 316, to avoid any vessel in the vessel map. An indicator is computed (step S806). It may be an indicator of at least one of speed of displacement, the temporal variance, and the spatial variance. If speckle tracking is not currently being utilized for the acoustic streaming testing, or if it is not multi-dimensional speckle tracking (step S808), compare the indicator to a threshold to determine whether the material 324 tested is liquid (step S810). If the indicator does not exceed the threshold (step S810), the material 324 is determined to be solid (step S812). Otherwise, if the indicator exceeds the threshold, the material 324 is determined to be liquid (step S814). At this point, in this or any other testing technique, return can be made to the start of the routine for more testing in a different spatial part of the current hypoechoic area 210. Although, this single determination suffices to conclude that the current hypoechoic area 210 is liquid, or is assumed to be liquid subject to a different determination based for example on the optional and confirmatory attenuation readings discussed herein above. Continuing on, if, on the other hand, multi-dimensional speckle tracking is being used (step S808), and the indicator does not exceed the randomness threshold $T_R$ 428 (step S816), the material 324 is determined to be solid (step S812). Otherwise, if $T_R$ is exceeded (step S816), the material 324 is determined to be liquid (step S814).

If speed of displacement is not the current testing technique (step S802), the next alternative may apply. In particular, if temporal variance is the current testing technique (step S820), the above-mentioned special testing sequence is issued (step S822). The respective indicator is computed (step S824). If the indicator does not exceed a temporal variance threshold $T_{TV}$ (step S826), the material 324 is deemed to be solid (step S812). Otherwise, if $T_{TV}$ is exceeded (step S826), the material 324 is deemed to be liquid (step S814).

If spatial variation is the current testing technique (step S828), processing branches to step S822, although a spatial variance threshold $T_{SV}$ is used in step S826 instead of $T_{TV}$.

If signal-to-background ratio (SBR) is the current testing technique (step S830), the imaging depth range 508 of relatively low echo intensity is identified (step S832). For the current imaging frame, or time period, 228, the accumulated displacement in the range 508 and outside are measured (step S834). The accumulated SBR 520 is formed (step S836). It is plotted or otherwise linked to the current time period 228, and thus plotted repeatedly as time progresses (step S838). If a next time period is to be processed (step S840), return is made to the displacement measuring step S834. Otherwise, if no next time period is to be processed (step S840), and if graph slope is the criterion (step S842), it is checked whether the graph slope, after a predetermined number of initial frames or time periods 228, exceeds a slope threshold $T_S$ (step S844). If $T_S$ is not exceeded (step S844), the material 324 is deemed to be solid (step S812). Otherwise, if $T_S$ is exceeded (step S844), the material 324 is deemed to be liquid (step S814). If, on the other hand, graph slope if not the criterion (step S842), then graph straightness is the criterion in which case it is checked whether straightness of the graph exceeds a straightness threshold $T_{ST}$ (step S846). A linear regression can, for example, be calculated based on the plotted data, and absolute deviations of the plotted data from the regression line can be summed to assess straightness. If $T_{ST}$ is not exceeded (step S846), the material 324 is deemed to be solid (step S812). Otherwise, if $T_{ST}$ is exceeded (step S846), the material 324 is deemed to be liquid (step S814). Optionally, both straightness and the slope of the graph can be considered.

If decorrelation is the current testing technique (step S848), tissue displacement 226 caused by a push is tracked for a given moment in time (step S850). For that moment, the maximum correlation coefficient 224 is detected (step S852). The detected coefficient 224 is compared to the correlation coefficient threshold $T_{CC}$ (step S854). If $T_{CC}$ is exceeded (step S854), the material 324 is deemed to be solid (step S812). Otherwise, if $T_{CC}$ is not exceeded (step S854), the material 324 is deemed to be liquid (step S814).

If relative motion magnitude is the current testing technique (step S848), soft tissue adjacent to the current candidate hypoechoic area 210 is detected (step S856). The detection may be based on brightness, since bone and other hard body tissue tend to be considerably more echogenic. Acoustic streaming pushes are issued to both the candidate area 210 and to the soft tissue detected (step S858). Immediately corresponding tracking pulses 350, of equal acoustic power, are emitted (step S860). Relative motion, as between the area 210 and the soft tissue, is compared (step S862). If motion of the area 210 does not exceed that of the soft tissue by at least a relative motion threshold $T_{RM}$ (step S864), the material 324 in the area 210 is deemed to be solid (step S812). Otherwise, motion of the area 210 does exceed that of the soft tissue by at least the relative motion threshold $T_{RM}$ (step S862), the material 324 in the area 210 is deemed to be liquid (step S814).

Any one or combination of the above-described testing techniques may be utilized.

Ultrasound-based acoustic streaming for deciding whether material is fluid is dependent upon any one or more of a variety of criteria. Examples are displacement, speed, temporal or spatial flow variance, progressive decorrelation, slope or straightness of accumulated signal to background comparisons over time, and relative displacement to adjacent soft tissue. Echogenicity-based area identification is combinable with the above movement characteristic detection in the deciding. Fluid pool identification is performable from the area-limited acoustic streaming testing and ultrasound attenuation readings. Candidates from among the areas are screenable based on specific shapes or bodily organs detected. Natural flow can be excluded from streaming detection by identification of blood vessels. Processing for each FAST ultrasound view, or for the entire procedure, is performable automatically, without need for user intervention or with user intervention to identify suspected areas.

Although the above discussion is in the context of medical applications, what is proposed herein above is not limited to this area and may, for example, find application is guiding acoustophoresis. Nor is chest or abdominal trauma a limitation. Methodology proposed herein above is usable, for instance, in intracranial examination. Nor is trauma a limitation. It is within the intended scope of what is proposed herein above that above-described techniques be used in periodic medical examination. What is proposed may be utilized in vivo or ex vivo. Although blood pools is a focus, other fluid accumulation inside the body may also be detected and spatially defined. The above-noted flexibility as to platform of implementation suggests the wide variety of applications.

While the invention has been illustrated and described in detail in the drawings and foregoing description, such illustration and description are to be considered illustrative or exemplary and not restrictive; the invention is not limited to the disclosed embodiments.

For example, in the case of the matrix, or "two-dimensional", array, it may be used for interrogating multiple regions simultaneously.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The word "exemplary" is used herein to mean "serving as an example, instance or illustration." Any embodiment described as "exemplary" is not necessarily to be construed as preferred or advantageous over other embodiments and/or to exclude the incorporation of features from other embodiments. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. An apparatus configured for deciding whether material that is in an ultrasound medium is fluid comprising:
   an ultrasound image acquisition system comprising an ultrasound imaging probe; and
   an ultrasound image analysis system, the ultrasound image analysis system comprising at least one processor circuit configured to perform image segmentation to detect and define a hypoechoic area depicted in an ultrasound image of a body, wherein the hypoechoic area includes said material,
   wherein the ultrasound imaging probe is configured to issue an acoustic wave in the hypoechoic area defined by the ultrasound image analysis system, the acoustic wave propagating in an axial direction which is transverse to a lateral direction to cause bulk movement of said material in a sound field created by transfer of energy from said acoustic wave, wherein said ultrasound imaging probe is further configured to induce in said material flow speeds that vary spatially and temporally via said acoustic wave; and
   wherein the at least one processor circuit is further configured to:
   responsive to said ultrasound image acquisition system subjecting said material to said acoustic wave, compute an estimate for said material that includes an indicator of spatial variance of the flow speeds, wherein said spatial variance is in said lateral direction, and
   decide whether the material that is in the ultrasound medium is fluid based on said estimate.

2. The apparatus of claim 1, wherein said deciding comprises comparing said indicator to a spatial variance threshold.

3. The apparatus of claim 1, wherein the ultrasound image acquisition system is configured to emit multiple push pulses for said inducing,
   wherein multiple tracking pulses are emitted following said push pulses, wherein not all of said multiple tracking pulses are emitted in a same direction.

4. The apparatus of claim 1, further comprising a user interface configured to receive user input.

5. The apparatus of claim 1, wherein said processor circuit is further configured for:
   identifying a blood vessel in said ultrasound image of the body that includes said material; and
   identifying a stationary pool of liquid in said body, wherein said identifying of the pool comprises said deciding, wherein said identifying of the pool takes into account the identification of the blood vessel.

6. A method for deciding whether a material that is in an ultrasound medium is fluid, the method comprising:
   performing image segmentation to detect and define a hypoechoic area depicted in an ultrasound image of a body wherein the hypoechoic area includes the material;
   issuing, with an ultrasound imaging probe, an acoustic wave in the hypoechoic area defined in the ultrasound image, the acoustic wave propagating in an axial direction which is transverse to a lateral direction;
   responsive to the acoustic wave, computing an estimate that includes an indicator of spatial variance of speed of the acoustic wave propagating in the material, wherein the spatial variance is in the lateral direction; and
   deciding whether the material that is in the ultrasound medium is a fluid based, at least in part, on the estimate.

7. The method of claim 6, wherein the deciding comprises comparing the indicator to a spatial variance threshold.

8. The method of claim 6, wherein the issuing comprises emitting multiple push pulses and the method further comprises emitting multiple tracking pulses following the push pulses, wherein not all of the multiple tracking pulses are emitted in a same direction.

9. The method of claim 6, further comprising:
   identifying a blood vessel in the ultrasound image of the body; and
   identifying a stationary pool of liquid in the body, wherein the identifying of the pool comprises the deciding, wherein the identifying of the pool takes into account the identification of the blood vessel.

10. A non-transitory computer readable medium including instructions that when executed cause an ultrasound imaging system to:
    perform image segmentation to detect and define a hypoechoic area depicted in an ultrasound image of a body wherein the hypoechoic area includes a material;
    issue an acoustic wave in the hypoechoic area defined, the acoustic wave propagating in an axial direction which is transverse to a lateral direction;
    responsive to the acoustic wave, compute an estimate that includes an indicator of spatial variance of speed of the acoustic wave propagating in the material, wherein the spatial variance is in the lateral direction; and
    decide whether the material is a fluid based, at least in part, on the estimate.

11. The non-transitory computer readable medium including instructions of claim 10, wherein the non-transitory computer readable medium further includes instructions that when executed cause the ultrasound imaging system to issue ultrasound signals to acquire the ultrasound image of the body.

* * * * *